United States Patent [19]

Sun et al.

[11] Patent Number: 4,762,888

[45] Date of Patent: Aug. 9, 1988

[54] HOT MELT PRESSURE SENSITIVE ADHESIVES

[75] Inventors: Robert L. Sun, Stanhope; James F. Kenney, Mendham, both of N.J.

[73] Assignee: Johnson & Johnson Products, Inc., New Brunswick, N.J.

[21] Appl. No.: 2,316

[22] Filed: Jan. 12, 1987

Related U.S. Application Data

[63] Continuation-in-part of Ser. No. 634,716, Jul. 26, 1984, abandoned.

[51] Int. Cl.$^4$ ............... C08L 33/08; C08L 33/10; C08L 75/04
[52] U.S. Cl. ................... 525/125; 525/217; 560/166; 604/358
[58] Field of Search ................ 525/217, 125

[56] References Cited

U.S. PATENT DOCUMENTS 4,045,517 8/1977 Guerin et al. ............... 525/217
4,495,243 1/1985 Kishi ............... 525/217

FOREIGN PATENT DOCUMENTS 54-108483 8/1979 Japan ............... 525/217

*Primary Examiner*—Jacob Ziegler

[57] ABSTRACT

What is disclosed are novel hot melt adhesives having pressure sensitive properties that are comprised of a combination of two acrylic-based copolymers containing the novel monomer 1(2)-methyl-3-oxa-4-oxo-5-azanonyl methacrylate, one of the copolymers being a low glass transition temperature (Tg) copolymer and the other a high Tg copolymer and which hot melt adhesives, by means of reversible hydrogen bond formation and dissociation, possess the reversible properties of providing a strong cohesive strength at ambient temperature but also having a melt viscosity at elevated coating temperatures such that it can be used in hot melt coating equipment; a process for making said hot melt adhesives; and a process for making adhesive tapes and bandages using said adhesives.

2 Claims, No Drawings

HOT MELT PRESSURE SENSITIVE ADHESIVES

CROSS REFERENCE

This is a continuation-in-part of application Ser. No. 634,716, filed July 26, 1984, now abandoned.

This invention relates to improved surgical pressure sensitive hot melt adhesives, and to adhesive sheet products such as adhesive tapes and adhesive bandages, utilizing said hot melt adhesives that adhere to human skin and remain adherent. In particular, it relates to novel hot melt adhesives having pressure sensitive properties that are comprised of a combination of two acrylic-based copolymers, each containing 1(2)-methyl-3-oxa-4-oxo-5-aza-nonyl methacrylate as a monomer, one of the copolymers being a low glass transition temperature (Tg) copolymer and the other a high Tg copolymer; which hot melt adhesives by means of reversible hydrogen bond formation and dissociation possess the reversible properties of strong cohesive strength at ambient temperature and desirable melt viscosity at elevated coating temperatures. The invention provides a process for making the hot melt adhesive as well as a process for making adhesive tapes and bandages. This invention also relates to the novel compound, 1(2)-methyl-3-oxa-4-oxo-5-aza-nonyl methacrylate, which is used as a monomer to make the adhesives of this invention.

BACKGROUND OF THE INVENTION

Hot melt pressure sensitive adhesives are 100 percent solid materials; and therefore, no solvent or water removal is required in coating operations. Also, they require a fraction of the energy required by solvent and water-based systems during coating operations. Hot melt adhesives are applied in a molten state to a backing and are then cooled rapidly with the help of a chill roll. Coating operations can be carried out at higher speeds with less equipment, lower energy cost, and greater safety than with solvent or water-based adhesives. Hot melt coating technology offers superior economics to solvent or water-based coating.

There are three classes of hot melt pressure sensitive adhesives:
1. formulated polyethylene copolymers
2. synthetic thermoplastic rubber elastomers formulated with tackifiers and
3. polyacrylates.

To date, the multi-component systems, especially the thermoplastic rubber with additives, have received more attention because of their availability, low cost and flexibility of formulation. On the other hand, the acrylic hot melt adhesives have deficiencies in that they exhibit an undesirable melt temperature/viscosity profile, unbalanced adhesive properties, and often require additives to modify the acrylic polymer in order to have acceptable performance.

Many hot melt adhesives presently available are blends of thermoplastic elastomers with plasticizer and tackifier resins derived from natural resins. These adhesives generally exhibit poor clarity, are discolored and often irritate the skin, which are undesirable for surgical tape products. Many of the elastomers used in these hot melt adhesives contain unsaturated chemical bonds, e.g., styrene-isoprene-styrene and styrene-butadiene block copolymers; these bonds are attacked by oxygen and ultraviolet radiation resulting in loss of adhesive properties. Prior art acrylic hot-melt pressure sensitive adhesives have been prepared by utilizing nonpermanent intermolecular cross-linking. A conventional solvent or water-based 100% solids acrylic pressure sensitive adhesive is far from being sufficiently fluid at the coating temperatures required for hot melt adhesives.

Hot melt adhesives based on the principle of crystallization to control adhesive viscosity almost always require long sequences of methylene groups which act to increase the effective molecular weight at low temperature. However, a balanced ratio between the crystalline domains and amorphous regions is essential. At higher crystalline content, an adhesive tends to lose its tackiness due to phase separation whereas at a lower crystalline content an adhesive of low cohesive strength is obtained.

In the past, attempts have been made to produce acrylic-based hot melt adhesives by incorporating 0.5 to 25% by weight of metallic chelating agents, such as zinc or cadmium salts to an amine-containing copolymer. The thus produced adhesives possess non-permanent, reversible bonds and showed an increase in Williams Plasticity number from 0.93 to 1.25 mm (U.S. Pat. No. 3,925,282).

Another method found in the patent literature for improving cohesive strength of acrylic-based hot melt adhesives is blending two copolymers, one copolymer containing a tertiary amine group, and the other has a built-in organic acid group. Upon mixing, a reversible ionic bonding is formed. (U.S. Pat. No. 4,045,517).

An improved hot melt pressure sensitive adhesive requires higher Williams Plasticity number to avoid cold flow. An adhesive for medical usage generally has higher requirements, such as no skin irritation, clarity, colorless, and higher moduli for lower adhesive transfer to skin. Hot melt adhesives made from amine-containing monomers have high tendency of discoloring, and metallic chelating agents may cause skin irritation. Currently available hot melt pressure sensitive adhesives exhibit acceptable tack, however, the cold flow, creep resistance and low modulus properties need improvement.

The novel hot melt pressure sensitive adhesives of this invention utilize a novel acrylic monomer, 1(2)-methyl-3-oxa-4-oxo-5-aza-nonyl methacrylate, and contain neither organic amine nor acid functional groups, nor metallic salts. The hot melt adhesives of this invention are comprised of a combination of two acrylic-based copolymers, one of which copolymers is a low glass transition temperature (Tg) copolymer, while the other is a high Tg copolymer. Each of these copolymers uses as a comonomer the novel compound 1(2)-methyl-3-oxa-4-oxo-5-aza-nonyl methacrylate which exists in two isomeric forms, as depicted below:

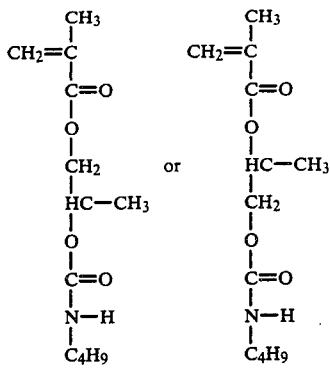

For purposes of the present invention, either isomeric form, or a mixture of both, can be used as one of the co-monomers.

The pressure sensitive adhesives of the present invention differ from the prior art. Hot melt pressure sensitive adhesive compositions are disclosed in U.S. Pat. Nos. 4,045,517; 3,925,282; and 4,164,614. The closest known art is U.S. Pat. No. 4,045,517 (1977) of Guerin, Hutton, Miller and Zdanowski assigned to Rohm and Haas Company. This patent discloses novel polyacrylic hot melt adhesives prepared by blending a polymer having a Tg of −85° to 10° C. with a polymer having a Tg of 20° to 150° C. The hot melt adhesives contain carboxylic acid, sulfonic acid or amine groups.

U.S. Pat. No. 3,925,282 (1975) (Davis, Skoultchi and Fries), National Starch and Chemical Corporation, discloses a hot melt adhesive composition which possesses the reversible properties of strong cohesive strength at ambient temperatures and desirable melt viscosity at application temperatures and which is prepared by the reaction of a normally tacky acrylic-based random copolymer containing a tertiary amine-containing monomer with an organic metallic salt comprising a transition metal, tin or lead as the metallic component and an organic acid anion. The random copolymers are capable of forming reversible coordinate cross-links on the addition of small amounts of selected organic metallic salts.

U.S. Pat. No. 4,164,614 (1979) (W. A. Ames), Eastman Kodak Company, discloses hot melt adhesive composition comprising terpolymers containing 2-ethylhexyl acrylate, N-vinyl-2-pyrrolidone and styrene. The terpolymers can be applied to tapes or labels.

In addition, U.S. Pat. No. 4,337,325 (1982) (K. Shah), Kendall Company, discloses pressure-sensitive adhesive compositions comprising a blend of copolymers consisting of acrylic monomers and vinyl lactam. The copolymer adhesive blend exhibits a viscosity less than 100,000 cps at 350° F.

STATEMENT OF THE INVENTION

The acrylic hot melt pressure sensitive adhesive of the present invention possesses high adhesive strength to human skin and high cohesive strength such that it remains adhered to skin, and yet on voluntary removal only negligible adhesive transfer to skin occurs. It is comprised of a combination of two acrylic-based co-polymers, each containing a 1(2)-methyl-3-oxa-4-oxo-5-aza-nonyl methacrylate monomer. This monomer is a novel compound, and constitutes another aspect of the invention.

Since this invention relates to surgical hot melt pressure sensitive adhesives and more particularly to hot melt pressure sensitive adhesives and hot melt adhesive-coated products that are adapted to be secured to the human skin, it is, accordingly, an object of the present invention to prepare acrylate hot melt pressure sensitive adhesives having good skin adherence.

A still further object of the present invention is the development of a process for making the adhesive. A yet further object of the present invention is the development of surgical pressure sensitive adhesive sheet products.

Surgical pressure sensitive adhesive sheet products, as the term is herein used, include any product having a flexible backing and a pressure sensitive adhesive coating hereon and includes, although it is not limited to, such products as adhesive tapes, adhesive bandages, adhesive plasters, adhesive-coated surgical operating sheets, adhesive-coated corn pads, adhesive-coated absorbent dressings, and the like.

DETAILED DESCRIPTION OF THE INVENTION

The hot melt adhesives of this invention are comprised of a combination of two acrylic-based copolymers, each of which contains the novel compound of this invention, 1(2)-methyl-3-oxa-4-oxo-5-aza-nonyl methacrylate. This compound which is used as a monomer herein is a novel compound that exists in two isomeric forms, as depicted below:

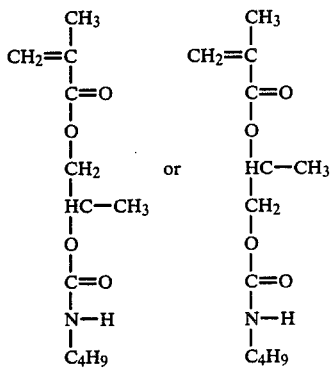

For purposes of the present invention, either isomeric form, or a mixture of both, can be used. This novel monomer, when incorporated in the polymer chain, is capable of forming hydrogen bonding inter- or intramolecularly.

The principle of intermolecular or intramolecular hydrogen bonding is used to control adhesive viscosity, cohesive strength, moduli and Williams Plasticity number.

It has been found that when acrylic monomers are copolymerized with the 1(2)-methyl-3-oxa-4-oxo-5-aza-nonyl methacrylate monomer which is capable of forming H-bonding, there is a significant increase in the cohesive strength of the hot melt adhesive. At room temperature the H-bonding sites function as cross-links between polymer chains. At the coating temperature, the H-bonds are dissociated or broken, resulting in an adhesive with low melt viscosity suitable for coating on a substrate. The hot melt pressure sensitive adhesives with hydrogen bonding-forming monomer perform especially well when the adhesive is comprised of a blend or two copolymers both of which contain hydrogen bonding monomer. One copolymer has a lower molecular weight and a glass transition temperature (Tg) above 10° C., preferably 25° to 60° C. The other copolymer comprising the hot melt adhesive has a higher molecular weight and a lower glass transition temperature, lower than −20° C. preferably −30° to −80° C. For convenience the two copolymers will be differentiated as being either a "high Tg copolymer" or a "low Tg copolymer" for purposes of the present invention.

The preferred hot melt adhesive compositions comprise a blend of:

1. from 15 to 30 parts by weight of a high Tg copolymer having a Tg in the range of from about 10° C. to about 100° C. containing from 5 to 15 part of hydrogen bond-forming monomer, namely, 1(2)-methyl-3-oxa-4-oxo-5-aza-nonyl methacrylate and 85 to 95 parts of alkyl esters of methacrylic acid, wherein said alkyl group contains 1 to 12 carbon atoms. Such alkyl esters include methyl methacrylate, ethyl methacrylate, n-propyl methacrylate. iso-propyl methacrylate, n-butyl methacrylate, isobutyl methacrylate, sec-butyl methacrylate, t-butyl methacrylate, iso-pentyl and cyclohexyl methacrylate.

2. from 70 to 85 parts by weight of low Tg copolymer having a Tg in the range of about −20° C. to about −80° C. containing from 5 to 15 parts of hydrogen bond-forming monomer namely, 1(2)-methyl-3-oxa-4-oxo-5-aza-nonyl methacrylate and 85 to 95 parts of alkyl esters of acrylic acid, wherein said alkyl group contains 4 to 12 carbon atoms. Such alkyl esters include n-butyl acrylate, n-pentyl acrylate, n-hexyl acrylate, n-heptyl acrylate, n-octyl acrylate, n-nonyl acrylate, n-decyl acrylate, n-undecyl acrylate, n-dodecyl acrylate and their branched isomers such as 2-ethylhexyl acrylate.

Especially preferred are hot melt adhesive compositions containing a blend of:

1. from 70 to 85 parts by weight of a low Tg copolymer made from 5 to 15 parts by weight of 1(2)-3-oxa-4-oxo-5-aza-nonyl methacrylate monomer and 85 to 95 parts by weight of a comonomer selected from one or more of the following:
n-butyl acrylate, ethyl acrylate, methyl acrylate, or 2-ethylhexyl acrylate.

2. from 15 to 30 parts by weight of a high Tg copolymer made from 5 to 15 parts by weight of 1(2)-methyl-3-oxa-4-oxo-5-aza-nonyl methacrylate monomer and 85 to 95 parts by weight of comonomer selected from one or more of the following:
n-butyl methacrylate, isobutyl methacrylate, t-butyl methacrylate or isopropyl methacrylate.

Polymerization may be carried out by solution, emulsion, suspension or in bulk. For easy of bending, solution polymerization is preferred. Catalysts generally used in polymerizations such as peroxy ester, azo compounds or peroxides are suitable for polymerization. The amount of catalyst used is preferably between 0.5 to 8% based on the total monomer weight. The preferred catalysts are benzoyl peroxide, t-butyl perbenzoate, t-butyl peroxtoate, t-butyl perpivalate, lauroyl peroxide, dicumyl peroxide, azobisisobutynonitrile, and 2,2'-azobis(2,4-dimethylvaleronitrile).

The moduli and melt viscosity of the hot melt adhesive can be controlled by varying the ratio of the copolymer blend comprising the adhesive to suit the special product application of the adhesive. Williams plasticity can be controlled by varying the copolymer blend ratio as well. To illustrate, an 18% by weight of high glass transition temperature (Tg) copolymer blended with 82% by weight of low glass transition temperature copolymer exhibits a Williams plasticity number of 1.3 mm, when the copolymer blend is increased to 25% by weight of high glass transition temperature copolymer the Williams plasticity number increases to 1.7 mm. The 75/25 copolymer adhesive blend on heating exhibits good melt processing characteristics, the melt viscosity being as follows:
176,000 cp at 300° F.
54,000 cp at 350° F.
21,000 cp at 400° F.

The melt viscosities were determined in a Thermosel viscometer.

The hot melt adhesive of this invention is evaluated by coating the adhesive on a backing material on a hot melt coating machine, making tapes and wear performance testing of the tapes on human subjects. For surgical tape application, various baking materials are used, such as cloth, paper and plastic films. The surgical tape or a first-aid tape provided in this invention has the following backing materials. For absorbent type backings, they can be wood pulp fibers, rayon, polyester, acetate fibers, cotton fibers and blend combinations such as wood pulp and rayon, and wood pulp and polyester. Plastic backings can be polyvinyl chloride, polyethylene, polypropylene, Mylar and the like. The backing for the tape depends on the application.

The tapes made with the hot melt adhesives of this invention are compared in wear performance with commercial surgical adhesive tapes. The hot melt adhesive tapes of this invention exhibit higher adhesion and lower adhesive transfer to skin than commercial adhesive tapes.

The invention will be described in greater detail by the following examples in which all parts are by weight. As a quantitative aid to evaluating products of the present invention, it has been found helpful to employ certain empirical tests, which will be described in more detail.

Williams Plasticity Number—This property is measured by the use of a Williams Plastometer which is manufactured by Scott Tessters, Inc. and is designed to conform to the standards set by ASTM Method D-926.

Wear Performance Test—Adhesion to Skin, 24-Hour Arm Test, Panel—24 Subjects. Procedure—Six to eight 1×3" strips of adhesive rotated so that each sample is in each position an equal number of times. There are no restrictions on normal activities and bathing habits. At the end of 24 hours, adhesion readings are taken. Skin redness, degree of skin strippage and adhesive left on the skin are noted and recorded. The rating and scoring of adhesion and adhesive transfer are recorded as:

| Adhesion Rating Scale | Adhesion Scoring Scale |
| --- | --- |
| 0 = Adhesive tape off | 0 |
| 1 = Hanging - ¾ off | 0 |
| 2 = Hanging - ⅜ off | 0 |
| 3 = One or both end flaps up ½ | 3 |
| 4 = One or both end flaps up ⅛ | 3 |
| 5 = One or more end corners up ¼ | 7 |
| 6 = One corner up slightly | 10 |
| 7 = perfect adhesion | 10 |
| Adhesive Transfer Rating Scale | Adhesive Transfer Scoring Scale |
| 0 = No residue | 0 |
| 0.5 = Trace amount of residue | 1 |

| | |
|---|---|
| 1.0 = Thin Presence of residue | 4 |
| 1.5 = Marked, specific amount of residue | 4 |
| 2.0 = Heavy residue | 10 |

Data are analyzed on average rating and average score. For example, for 24 subjects, all score 7 in adhesion, average adhesion will be 100% and average score will be 7.

Modulus Measurement

Rheometrics Dynamic Spectrometer (RDS) is used to determine adhesive viscoelastic behavior in terms of storage (G') and loss (G") moduli at a wide range of oscillation frequency and temperature. RDS is manufactured by Rheometrics, Inc. in Union, N.J. It uses oscillatory shear over a wide range of frequency, temperature, and amplitude to measure the response or deformaion of the polymer. The deformation (response) is printed by a Texas Instrument Model 700 terminal. Storage, loss and complex moduli are calculated. Also, the ratio G" to G', which is tan δ, is computed. Oscillation frequency can be varied from 0.01 to 500 rad/sec. Temperature can be incrementally varied over the range of −150° to 400° C., and temperature and frequency sweeps can be combined. For this invention, the adhesive was examined under frequency sweep from 0.1 to 300 rad/sec at 15% strain rate and constant temperature. Five temperatures, 25°, 36°, 60°, 90° and 120° C. were selected to run each frequency sweep separately. Dynamic storage modulus (G') and loss modulus (G") were plotted against the frequency range at one of the above four temperatures on log-log graph paper. Time temperature superposition principle is applicable to the adhesive compositions. A master graph is constructed by shifting modulus curves of 26°, 60°, 90° and 120° C. to modulus curve of 36° C. (human body temperature). The modulus data at the frequency range below 0.1 rad/sec are gathered from the measurement at 90° and 120°. C. At the frequency range between 0.1 to 300 rad/sec modulus data are generated from all four temperatures.

Example 1 illustrates the method of preparation of 1(2)-methyl-3-oxa-4-oxo-5-aza-nonyl methacrylate monomer which is useful in the preparation of copolymers illustrated in Examples 2–6 which in turn are useful in the preparation of hot melt adhesives and various surgical tape products coated with said adhesives as illustrated in Examples 7–11. Instead of preparing the Low Tg copolymer and the High Tg copolymer separately, and then blending them to make the final adhesive composition, it is possible to prepare the final adhesive sequentially in the same reactor. This is done by first preparing either one of the copolymers, then adding the monomers needed for the other copolymer, and reacting them in the same reactor, as illustrated by Examples 4 and 5.

EXAMPLE 1

Preparation of 1(2)-Methyl-3-oxa-4-oxo-5-aza-nonyl Methacrylate

Butyl isocyanate (167.07 parts), toluene (455.60 parts) and di-t-butyl hydroquinone (0.03371 part) were placed in a reaction flask which was equipped with mechanical stirrer, thermometer, nitrogen inlet and dropping funnel. A solution of hydroxypropyl methacrylate (242.69 parts) and stannous octoate (T-9) (0.3371 part) in toluene (134.27 parts) was slowly added into the flask over a period of 30 minutes. The temperature was maintained at 20° C. After the addition was over, the solution was heated to 50° C. for 7 hrs. or until all the isocyanate group was all consumed. After the reaction was completed, toluene was removed by applying vacuum to the flask. The product was a clear liquid with a boiling point of 105° C. at 0.25 mm vacuum. The IR spectrum of the product exhibited absorptions at 3380 cm$^{-1}$ (N—H), 1735 cm$^{-1}$

1720 and 1570 cm$^{-1}$ (urethane). The proton nmr spectrum of the compound in chloroform-d gave absorptions at δ=6.12 (1H), 5.58 (1H) 4.68–5.42 (1H), 4.18 (2H), 3.15 (2H), 1.94 (3H) and 0.67–1.62 (7H).

EXAMPLE 2

Preparation of Poly(isobutyl methacrylate/1(2)-methyl-3-oxa-4-oxo-5-aza-nonyl Methacrylate)

To a 4000 ml reaction kettle equipped with a condenser, thermometer, nitrogen inlet and mechanical stirrer were added toluene (236.34 parts), monomer mix (98.48 parts) which was prepared by mixing isobutyl methacrylate (623.69 parts) with 32.83 parts of 1(2)-methyl-3-oxa-4-oxo-5-aza-nonyl methacrylate of Example 1. The reaction kettle was heated to 115° C., then 11.82 parts of catalyst solution (8.67 parts of t-butyl peroctoate in 98.48 parts of toluene) were added to the reaction kettle. After polymerizing for 30 minutes at 115° C., the remaining 558.04 parts of monomer mix and 63.03 parts of catalyst solution were added to the kettle simultaneously over a period of 3 hrs. After the addition was over, the polymerization was held for an additional 30 minutes at 115° C. The remaining catalyst solution was then added dropwise to the solution in 30 minutes. After the addition was over, the polymer solution was held for 30 minutes at 115° C. The polymer solution was cooled to room temperature and discharged from the reactor. The viscosities of the solution were measured at 70°, 150° and 250° F. as 170,000, 6,000 and 1,500 cps, respectively. The solventless polymer had viscosities of 140,000, 70,000 and 8,000 cps at 300°, 350° and 400° F., respectively. The copolymer had a Tg at 38° C.

EXAMPLE 3

Preparation of Poly(butyl acrylate/1(2)-methyl-3-oxa-4-oxo-5-aza-nonyl Methacrylate)

To a 4000 ml reaction kettle equipped with a condenser, thermometer, nitrogen inlet and mechanical stirrer were added toluene 142.6 parts and monomer mix 166.95 parts which was prepared by mixing butyl acrylate (641.71 parts) with 1(2)-methyl-3-oxa-4-oxo-5-aza-nonyl methacrylate (71.3 parts) of Example 1. The mixture was heated at 83° C. and 28.88 parts of catalyst solution (1.78 parts of lauroyl peroxide in 142.6 parts of toluene) were added to the flask. After 30 minutes at 83° C. the remaining monomer mixture and 57.76 parts of catalyst solution were added at a constant rate over a period of 3 hours at 83° C. After the addition was over the polymerization was allowed to continue at 83° C.

for 30 minutes. The remaining catalyst solution (57.8 parts) was added dropwise over a period of 30 minutes. The polymerization was continued for another 30 minutes and the polymer solution was discharged from the reaction kettle. The polymer solution had a viscosity of 286,000 cps at 71° F. and was 68.1% solid. The solventless polymer had a viscosity of 42,000 cps at 350° F. and Tg at −45° C.

EXAMPLE 4

Sequential Preparation of Poly(butyl acrylate/isobutyl methacrylate/1(2)-methyl-3-oxa-4-oxo-5-aza-nonyl Methacrylate)

To a 1-l four-neck round-bottom flask were placed 100 parts of toluene, 36.1 parts of butyl acrylate and 4 parts of 1(2)methyl-3-oxa-4-oxo-5-aza-nonyl methacrylate of Example 1. The reaction vessel was equipped with a mechanical stirrer, condenser, thermometer and nitrogen gas inlet and was heated to 83° C. by a heating bath. A solution made of 0.134 parts of lauroyl peroxide and 4 parts of toluene was added to the flask and the temperature was kept at 83° C. for 30 minutes. A solution of 204.54 parts of butyl acrylate, 22.72 parts of 1(2)-methyl-3-oxa-4-oxo-5-aza-nonyl methacrylate of Example 1, a mixture of 8 parts of toluene and 0.267 part of lauroyl peroxide were slowly added to the flask over a period of 2 hours. After the addition was over, the polymerization was allowed to continue for 20 minutes at 83° C. A mixture of 8 parts of toluene and 0.267 part of lauroyl peroxide were added to the reaction flask over a period of 10 minutes and the polymerization was continued for 20 minutes. The reaction temperature was then raised to 115° C. A solution of 77.962 parts of isobutyl methacrylate, 4.104 parts of 1(2)-methyl-3-oxa-4-oxo-5-aza-nonyl methacrylate of Example 1 and 0.6504 part of t-butyl peroctoate was slowly added to the polymerization vessel over a period of 40 minutes. After an additional 40 minutes, a catalyst solution of 0.4336 part of t-butyl peroctoate and 28.82 parts of toluene was added rapidly to the reaction vessel. The polymerization was held for an additional 30 minutes at 115° C. The polymer solution was discharged from the flask. The viscosity of the solution was 113,000 cps at room temperature. The solid hot melt adhesive polymer had a melt viscosity of 31,000 cps at 350° F.

EXAMPLE 5

Sequential Preparation of Poly(butyl acrylate/isobutyl methacrylate/1(2)-methyl-3-oxa-4-oxo-5-aza-nonyl methacrylate To a 500 ml four-necked round-bottom flask were placed 13.86 parts of dry toluene, 11.79 parts of isobutyl methacrylate and 2.08 parts of 1(2)-methyl-3-oxa-4-oxo-5-aza-nonyl methacrylate. The reaction flask was equipped with mechanical stirrer, condenser, thermometer and nitrogen gas inlet and was heated to 110° C. by a heating bath. A catalyst solution made of 0.03 part of t-butyl peroctoate and 2.77 parts of toluene was slowly added to the flask and the temperature was kept at 110° C. for 30 minutes. Then the bath temperature was reduced to 83° C. A solution of 47.14 parts of butyl acrylate, 8.32 parts of 1(2)-methyl-3-oxa-4-oxo-5-aza-nonyl methacrylate, 0.1 part of lauroyl peroxide and 9.70 parts of toluene were added dropwise to the reaction flask over a period of 4 hours. After the addition was over, the reaction mixture was allowed to stand for 30 minutes then 0.04 parts lauroyl peroxide in 4.16 parts toluene was added into the flask. The polymerization was held for an additional hour at 83° C. The polymer was discharged from the flask. The solid hot melt adhesive polymer had a melt viscosity of 60,000 cps at 350° F. and a Tg at −41° C.

EXAMPLE 6

Hot Melt Adhesive and Tape

Hot melt adhesives suitable for surgical tape applications were obtained by blending a solution of low Tg copolymer with a solution of high Tg copolymer. After thorough mixing, the solvent was removed under vacuum. The copolymer solution of Example 3 and the copolymer solution of Example 2 were physically blended at 50° to 70° C. in a ratio of 75 to 25, respectively, based on the percent solids in the solution. The solvent was stripped under vacuum. The solid hot melt adhesive had a Williams plasticity of 1.7 mm. The melt viscosities of the hot melt adhesive were determined with a Brookfield Thermosel Viscometer using Number 28 spindle and were 180,000 cps, 50,000 cps, and 20,000 cps at 300°, 350°, and 400° F., respectively. The dynamic mechanical properties of the adhesive were determined with a Rheometric Dynamic Spectrometer (RDS). The moduli (G' and G") vs frequency data are given in Table 1. The hot melt adhesive was coated on a rayon cloth taffeta surgical tape backing material on an Accumeter laboratory, bench-top hot melt coater. The coating temperature was 350° F. The hot melt adhesive was coated at 1.4 and 1.8 oz/yd$^2$, tapes made and wear performance evaluated. The results are shown in Table 2. The adhesive of this example was compared with commercial DERMICEL* Cloth Table sold by Johnson & Johnson Products, Inc., Covimax 472 emulsion adhesive sold by Franklin Chemical Industries and 2074 emulsion adhesive sold by Monsanto Company. The adhesive tape of this example exhibited excellent wear performance in skin adhesion and adhesive transfer (low).

EXAMPLE 7

Hot Melt Adhesive and Tape

The procedure of Example 6 was used to blend the copolymer solution of Example 3 and the copolymer solution of Example 2 in a ratio of 77 to 23, respectively. The solvent was stripped under vacuum. The solid hot melt adhesive had melt viscosities of 147,000, 44,000, and 19,500 cps at 300°, 350° and 400° F., respectively. The adhesive was coated on rayon cloth taffeta surgical tape backing material on an Accumeter hot melt coating machine. The coating temperature was 350° F. and the coating weights were 1.5 and 1.8 oz/yd$^2$. The wear performance was excellent in both skin adhesion and adhesive transfer. See Table 2.

EXAMPLE 8

Surgical Tape Made With Hot Melt Adhesive

The hot melt adhesive of Example 7 was coated on a paper surgical tape backing material on the Accumeter coating machine. The coating temperature was 350° F. and the coating weights were 1.2 and 1.5 oz/yd$^2$. The wear performance of the tapes was excellent in both skin adhesion and adhesive transfer. See Table 3. The adhesive of this example was compared with commercial Micropore Paper Table sold by 3M Company and DERMILITE* II Paper Tape sold by Johnson & Johnson Products, Inc.

EXAMPLE 9

Hot Melt Adhesive and Tape

The procedure of Example 6 was used to blend the copolymer solution of Example 3 and the copolymer solution of Example 2 in a ratio of 80 to 20 respectively. The solvent was stripped under vacuum. The solid hot melt adhesive had melt viscosities of 148,000, 46,000 and 19,300 cps at 300°, 350° and 400° F., respectively. The adhesive had a Tg of −45° C. The hot melt adhesive was coated at 350° F. on a rayon cloth taffeta backing material at 1.5 and 1.8 oz/yd². The wear performance was excellent in both skin adhesion and adhesive transfer. See Table 2.

EXAMPLE 10

Surgical Tape Made With Hot Melt Adhesive

The hot melt adhesive of Example 9 was coated on a paper surgical tape backing material according to the procedure of Example 8. The wear performance of the tapes was excellent in both adhesion to skin and adhesive transfer. See Table 3.

TABLE 1

Moduli vs Frequency of Example 6

| Frequency rad/sec. | $G^I$ (dynes/cm) | $G^{II}$ (dynes/cm) |
|---|---|---|
| 0.1 | $2.0 \times 10^5$ | $1.7 \times 10^5$ |
| 1 | $5.2 \times 10^5$ | $3.5 \times 10^5$ |
| 10 | $10.3 \times 10^5$ | $8.5 \times 10^5$ |
| 100 | $2.9 \times 10^6$ | $2.5 \times 10^6$ |
| 500 | $5.8 \times 10^6$ | $6.0 \times 10^6$ |

TABLE 2

Wear Performance of Adhesives on Rayon Cloth Backing

| Adhesive | Coating Weight oz/yd² | Average Adhesion | Adhesion % | Average Adhesive Transfer | Adhesive Transfer % |
|---|---|---|---|---|---|
| Example 6 | 1.4 | 6.4 | 95 | 0.6 | 15 |
| Example 6 | 1.8 | 6.3 | 92 | 0.6 | 14 |
| Example 7 | 1.5 | 6.8 | 96 | 0.6 | 16 |
| Example 7 | 1.8 | 6.9 | 100 | 0.6 | 17 |
| Example 9 | 1.5 | 6.7 | 100 | 0.6 | 15 |
| Example 9 | 1.8 | 6.5 | 96 | 0.6 | 15 |
| Control - Covinax 272 | 1.8 | 6.4 | 95 | 0.6 | 18 |
| Control - Emulsion Adhesive 2074 | 1.8 | 6.4 | 95 | 0.8 | 25 |
| Control - Solvent Based DERMICEL ™ Tape | 1.8 | 5.4 | 79 | 0.4 | 9 |

TABLE 3

Wear Performance of Adhesives on Paper Backing

| Adhesive | Coating Weight oz/yd² | Average Adhesion | Adhesion % | Average Adhesive Transfer | Adhesive Transfer % |
|---|---|---|---|---|---|
| Example 8 | 1.2 | 6.0 | 93 | 0.5 | 11 |
| Example 8 | 1.5 | 6.1 | 95 | 0.6 | 14 |
| Example 10 | 1.2 | 6.0 | 91 | 0.5 | 11 |
| Example 10 | 1.5 | 6.1 | 95 | 0.5 | 13 |
| Control - Micropore Paper Tape | — | 6.3 | 96 | 0.4 | 8 |
| Control - Dermilite ™ II Paper Tape | — | 5.8 | 87 | 0.4 | 8 |

We claim:

1. A hot melt pressure sensitive adhesive composition suitable for application to human skin, which by means of reversible hydrogen bond formation and dissociation possesses the reversible properties of both (i) strong cohesive strength at ambient temperature, and also (ii) a melt viscosity at elevated coating temperatures such that it can be used in hot melt coating equipment, said composition comprising:
   (A) from about 70 to 85 parts by weight of an acrylic copolymer having a low Tg in the range of from −20° C. to −80° C. comprising:
      (a) from 85 to 95 parts by weight of an alkyl acrylate monomer wherein the alkyl group contains 4 to 12 carbon atoms and
      (b) from 5 to 15 parts by weight of 1(2)-methyl-3-oxa-4-oxo-5-aza-nonyl methacrylate
   (B) from about 15 to 30 parts by weight of an acrylic copolymer having a high Tg in the range of from 10° C. to 40° C. comprising:
      (a) from about 85 to 95 parts by weight of an alkyl methacrylate monomer wherein the alkyl group contains 1 to 12 carbon atoms and
      (b) from about 5 to 15 parts by weight of 1(2)-methyl-3-oxa-4-oxo-5-aza-nonyl methacrylate.

2. An adhesive composition according to claim 1 wherein the alkyl acrylate monomer of Part (A) (a) is n-butyl acrylate, and wherein the alkyl methacrylate monomer of Part (B) (a) is isobutyl methacrylate.

* * * * *